(12) United States Patent
Nagata et al.

(10) Patent No.: US 8,110,362 B2
(45) Date of Patent: Feb. 7, 2012

(54) METHOD FOR DETERMINING A TONGUE CANCER

(75) Inventors: Masaki Nagata, Niigata (JP); Akira Kurokawa, Niigata (JP)

(73) Assignee: Niigata University, Niigata (JP)

( * ) Notice: Subject to any disclaimer, the term of this patent is extended or adjusted under 35 U.S.C. 154(b) by 375 days.

(21) Appl. No.: 12/445,222

(22) PCT Filed: Sep. 28, 2007

(86) PCT No.: PCT/JP2007/069075
§ 371 (c)(1),
(2), (4) Date: Apr. 10, 2009

(87) PCT Pub. No.: WO2008/044504
PCT Pub. Date: Apr. 17, 2008

(65) Prior Publication Data
US 2010/0068709 A1    Mar. 18, 2010

(30) Foreign Application Priority Data

Oct. 12, 2006   (JP) ................................. 2006-278203

(51) Int. Cl.
*C12Q 1/68* (2006.01)
(52) U.S. Cl. ..................................... 435/6.14; 435/6.12
(58) Field of Classification Search ........................ None
See application file for complete search history.

(56) References Cited

U.S. PATENT DOCUMENTS
7,108,969 B1    9/2006   Warrington et al.

FOREIGN PATENT DOCUMENTS
WO    2005/081867 A2    9/2005

OTHER PUBLICATIONS

Kim et al, Clin. Cancer res. 11: 79 (2005).*
Ahern, The Scientist 9 (15), 20 (1995).*
"Affymetrix GeneChip Human Genome U95 Version [1 or 2] Set HG-U95A" GEO Expression Host—GEO Expression, Mar. 11, 2002, XP002361325.
J. G. Eriksen et al., "Expression of integrins and E-cadherin in squamous cell carcinomas of the head and neck" APMIS, vol. 112, No. 9, Sep. 2004, pp. 560-568, XP002568370.
M. Nagata et al., "Identification of potential biomarkers of lymph node metastasis in oral squamous cell carcinoma by cDNA microarray analysis" International Journal of Cancer, John Wiley & Sons, Inc., US, CH, DE, vol. 106, No. 5, Jan. 1, 2003, pp. 683-689, XP003021374.
S. J. Wei et al., "Lymphatic metastasis is predicted by gene expression signature of the primary tumor in squamous cell carcinoma of the oral cavity" International Journal of Radiation: Oncology Biology Physics, Pergamon Press, USA, vol. 60, No. 1, Sep. 1, 2004, pp. S492.
R. K. O'Donnell et al., "Gene expression signature predicts lymphatic metastasis in squamous cell carcinoma of the oral cavity" Oncogene, Nature Publishing Group, GB, vol. 24, No. 7 Nov. 22, 2004, pp. 1244-1251, XP002332017.
C. E. Schmalbach et al., Molecular Profiling and the Identification of Genes Associated with Metastatic Oral Cavity/Pharynx Squamous Cell Carcinoma, Archives of Otolaryngology Head and Neck Surgery, American Medical Association, US, vol. 130, No. 3, Mar. 1, 2004, pp. 295-302, XP009054616.
Jan Nyman et al., "Prognostic factors for local control and survival of cancer of the oral tongue" Act Oncologia; 1993; 32(6) 667-73.
Kurokawa H et al., "The high prognostic value of the histologic grade at the deep invasive front of tongue squamous cell carcinoma" J. Oral Pathol Med; 2005. 34:329-33.
Okamoto M et al., "Prediction of delayed neck metastasis in patiens with stage I/II squamous cell carcinoma of the tongue", J. Oral Pathol Med 2002;31;227-233.
Xin Huang et al., "Serum proteomics study of the squamous cell carcinoma antigen in tongue cancer." J. Oral Oncology Jan. 2006:42; 26-31.
Akira Kurokawa et al., "Zetsugan Akuseido ni Kanrensuru Integrin Idensi Hatsygen no Kentto", Japanese Journal of Oral and Maxillofacial Surgery, Sep. 2006, vol. 52, Sokai Tokubetsugo, p. 198, 2-P3-04.
Masataka Nagata et al., "Zetsugan Sosgikinai Integrin Oyobi Tetraspanin Idenshigun no Akuseido Marker to shite no Yuyosei Kanto" Niigata Medical Journal , 2005, vol. 119; No. 12, p. 743, left column.
Masataka Nagata et al., Zetsugan no Integrin Kanren Idenshi Hatsugen Level ni yoru Akuseido Hantei, Japanese Journal of Oral and Maxillofacial Surgery, 2004 Nen, vol. 50, No. 13 (Sokaigo), p. 895-896, 2P19-2. Shinohara M et al., Expression of integrins in squamous cell carcinoma of the oral cavity (Correlations with tumor invasion and metastasis), Am. J. Clin. Pathol., 1999, 111(1), P75-88.

* cited by examiner

*Primary Examiner* — James Martinell
(74) *Attorney, Agent, or Firm* — McDermott Will & Emery LLP

(57) ABSTRACT

An object is to provide: a method for determining a tongue cancer in which the malignancy of tongue cancer can be objectively and accurately determined; a method for analyzing a tongue cancer tissue specimen; and a kit for analyzing a tongue cancer tissue specimen. There is provided: a method for determining a tongue cancer, comprising measuring mRNA quantity of an integrin family gene and a reference gene in the tongue cancer tissue specimen, and determining the malignancy of the tongue cancer based on a ratio of the mRNA quantity of the integrin family gene/the mRNA quantity of the reference gene; a method for analyzing a tongue cancer tissue specimen, comprising the steps of measuring mRNA quantity of an integrin family gene and a reference gene in the tongue cancer tissue specimen, and correlating a ratio of the mRNA quantity of the integrin family gene/the mRNA quantity of the reference gene with clinical data; and a kit for analyzing a tongue cancer tissue specimen.

7 Claims, 1 Drawing Sheet

METHOD FOR DETERMINING A TONGUE CANCER

CROSS-REFERENCE TO PRIOR APPLICATION

This is the U.S. National Phase Application under 35 U.S.C. §371 of International Patent Application No. PCT/JP2007/069075 filed Sep. 28, 2007, which claims the benefit of Japanese Patent Application No. 2006-278203 filed Oct. 12, 2006, both of which are incorporated by reference Jo herein. The International Application was published in Japanese on Apr. 17, 2008 as WO2008/044504 A1 under PCT Article 21(2).

BACKGROUND OF THE INVENTION

Field of the Invention

The present invention relates to a method for determining a tongue cancer in which the malignancy of tongue cancer is determined.

Tongue cancer is the most common in the oral cancer, with a high incidence of lymph node metastasis. Previous studies reported five-year survival rates of approximately 50% among patients without metastasis and approximately 11% among patients with metastasis including delayed metastasis (Jan Nyman et al. Prognostic factors for local control and survival of cancer of the oral tongue. *Act Oncologia;* 1993: 667-73). Tongue cancer tends to metastasize earlier in its clinical course than squamous cell carcinomas of other oral sites. Therefore, decision of the treatment regimen based on an accurate determination of the malignancy of tongue cancer, irrespective of the size of tumor, is essential not only for controlling the cancer but also from the viewpoint of QOL, which is influenced by post-treatment disorders of speech and swallowing.

Conventionally, histopathologic grade of differentiation (Kurokawa H. et al. The high prognostic value of the histologic grade at the deep invasive front of tongue squamous cell carcinoma. *J Oral Pathol Med.* 2005; 34: 329-33), degree of invasiveness (Kurokawa H. et al., 2005), conditions of lymph node metastasis (Kurokawa H. et al. 2005; Okamoto M. et al. Prediction of delayed neck metastasis in patients with stage I/II squamous cell carcinoma of the tongue. *J Oral Pathol Med.* 2002; 15: 227-233), the size of primary tumor (Kurokawa H. et al. 2005), serum tumor markers (Xin Huang et al. Serum proteomics study of the squamous cell carcinoma antigen1 in tongue cancer. *J Oraloncology.* 2006 January; 42(1): 25-30), and the like are used as prognostic factors of tongue cancer.

DISCLOSURE OF INVENTION

Problem to be Solved by the Present Invention

Such a histopathologic examination method is capable of detecting the presence or absence of oral cancer through morphological analysis of cancer tissue, however, it is poor in reliability and objectivity of information regarding the biological properties of oral cancer. Moreover, for a practical decision of the treatment regimen, the histopathologic examination method is not sufficient as a specific source of information of oral cancer, which covers an extremely wide variety of biological properties (the malignancy).

In addition, although the examination method using tumor markers can provide objective quantitative data, the data merely show the pathologic condition at the time of examination, with frequent false-positives and false-negatives. Thus, the examination method is not sufficiently reliable as an information source for the decision of the treatment regimen.

Therefore, in recent years, it has been hoped to realize practical characterization of tumor properties at the molecular level, although a concrete system for determination is still under construction.

Recently, matrix metalloproteinase family, cadherin family, integrin family, and the like, have been considered as candidate molecular-biological biomarkers of oral cancer. As mentioned above, the number of lymph node metastasis is epidemiologically closely related to the prognosis/outcome of the tongue cancer, and it is a simple and practical parameter for prognosis of the tumor malignancy.

Hence, use of appropriate molecules involved in the tissue reconstruction, cell adhesion, cell motility, and vascularisation, as biomarkers, will enable clinicians to make an accurate determination of the malignancy of the tongue cancer at an earlier stage than the onset of the metastasis. The accurate understanding of biological properties of early stage cancer will enable the optimization of treatment based on the information, which will bring about a great benefit.

Conventionally, determination of the malignancy of tongue cancer in terms of gene expression has not successfully attained the stage of practical application.

SUMMARY OF THE INVENTION

Therefore, it is an objective of the present invention to provide a method for determining a tongue cancer in which the malignancy of tongue cancer can be determined more objectively and accurately by using an integrin family gene as a biomarker and measuring the mRNA quantity or mRNA quantity of the integrin family gene.

The inventors of the present invention previously performed gene expression analysis of oral squamous cell carcinomas using a microarray. In the result, the integrin $\alpha 3$ and integrin $\beta 4$ genes exhibited significantly high expression levels in metastasis-positive tumors.

The integrin (ITG) molecules form a transmembrane-type heterodimer complex consisting of a $\alpha$ chain and a $\beta$ chain, the complex serving as a receptor connecting the cytoplasm and the extracellular matrix. ITG constitutes a superfamily of cell surface receptors which is involved in the adhesion to the extracellular matrix proteins such as fibronectin, collagens, and laminins, or platelets and leukocytes. Currently, human ITG have been cloned for eighteen genes of $\alpha$ chains and eight genes of $\beta$ chains, and twenty four species of receptors have been identified consisting of the $\alpha$ and $\beta$ chains. The extracellular domains of each receptor bind specifically to a particular extracellular matrix component ligand. 90% of the $\alpha$ and $\beta$ chain amino acid residues constitute an extracellular domain, and the rest of the amino acid residues constitute a short intracellular domain, which is bound to cytoskeletal actin fibers via cytoplasmic anchor proteins such as talin, paxillin, and $\alpha$-actinin. Apart from the role of adhesion molecules that connect extracellular ligands and the cytoskeleton, it has been known that ITG is involved in the cell motility, proliferation, differentiation and apoptosis by inducing tyrosine phosphorylation, change in the intracellular calcium concentration, inositol phospholipid synthesis, cyclin synthesis, and early gene expression in response to the signal from the extracellular matrix. In addition, some reports showed that cell differentiation and apoptosis are suppressed by blocking the interaction between ITG and ligand. It has been known that the loss of regularity in ITG molecule distribution in a tumor tissue correlates with its invasive/metastatic activity. Considering all of them, the disturbance of ITG-mediated adhesion and signaling is implicated in pathologic conditions such as development, growth, apoptosis, motility, and invasiveness of tumor cells in a variety of manners.

Therefore, based on the results of previously performed microarray analysis of gene expression, the inventors of the present invention saw a strong potential for integrin family genes as candidate biomarkers of the metastatic property and life prognosis of tongue squamous cell carcinoma. Quantitative real-time PCR gene expression analysis was performed on ITGα-1, -2, -3, -5, -6, and -v, and ITGβ-1, -3, -4, -5, and -6, which had been so far described to associate with the regulatory functions in adhesion, motility, and differentiation of tumor cells.

Incidentally, a tumor tissue is composed of tumor cells and various types of cells such as fibroblasts in the surrounding cancer stroma and inflammatory cells. Accordingly, it is anticipated that the cellular composition of cancer tissue has a great influence on the mRNA quantity of genes to be quantified. Therefore, normalization of the ITG gene expression level with the mRNA quantity of an appropriate gene is important for the analyses of biomarkers. As candidate molecule genes for normalization, not only so-called housekeeping genes, but also KRT5 which encodes epithelial cytoskeleton, JUP, PLEC1, and PXN which encode anchor proteins, LAMA3, LAMA4, LAMA5, Col1A1, and VTN which encode ligand molecules for ITGs were quantified in the same manner. An attempt has been made to circumvent problems caused by the variation among clinical specimens by normalizing the mRNA quantity of ITG genes with the mRNA quantity of genes which is relevant from the viewpoints of the function or the tissue localization.

Thus, as a result of intensive studies to address the above-mentioned problems, it was found out that the malignancy of tongue cancer can be objectively and accurately determined by measuring mRNA quantity of an integrin family gene and a reference gene, and using numeric values obtained through normalization of the mRNA quantity of the integrin family gene based on their ratio. This had led to the concept of the present invention.

The present invention provides a method for determining a tongue cancer, comprising measuring mRNA quantity of an integrin family gene and a reference gene in the tongue cancer tissue specimen, and determining the malignancy of the tongue cancer based on a ratio of the mRNA quantity of the integrin family gene/the mRNA quantity of the reference gene.

In the method for determining a tongue cancer of the present invention, the integrin family gene may be integrin α3 integrin β4, and/or integrin β5.

In the method for determining a tongue cancer of the present invention, the measurement of the mRNA quantity of the integrin family gene and the reference gene may be performed by real-time PCR analysis.

In the method for determining a tongue cancer of the present invention, the measurement of the mRNA quantity of the integrin family gene and the reference gene may be performed by Northern blot analysis or solid phase hybridization analysis.

In the method for determining a tongue cancer of the present invention, the reference gene may be a housekeeping gene, a cytoskeletal molecule gene, an anchor protein gene, and/or an extracellular matrix gene.

In the method for determining a tongue cancer of the present invention, the reference gene may be ACTB.

In the method for determining a tongue cancer of the present invention, the reference gene may be KRT5.

In the method for determining a tongue cancer of the present invention, the reference gene may be JUP and/or PXN.

The determination method of the present invention may be a method for determining tongue squamous cell carcinoma.

The present invention provides a method for analyzing a tongue cancer tissue specimen, comprising the steps of: measuring mRNA quantity of an integrin family gene and a reference gene in the tongue cancer tissue specimen; and correlating a ratio of the mRNA quantity of the integrin family gene/the mRNA quantity of the reference gene to clinical data.

In the method for analyzing a tongue cancer tissue specimen of the present invention, the clinical data may be composed of one or a plurality of type(s) of data selected from the group consisting of TNM classification, Y-K grade, response to chemotherapy, response to radiation therapy, and prognosis.

In the method for analyzing a tongue cancer tissue specimen of the present invention, the measurement of the mRNA quantity of the integrin family gene and the reference gene may be performed by real-time PCR analysis.

In the method for analyzing a tongue cancer tissue specimen of the present invention, the measurement of the mRNA quantity of the integrin family gene and the reference gene may be performed by Northern blot analysis or solid phase hybridization analysis.

In the method for analyzing a tongue cancer tissue specimen of the present invention, the integrin family gene may be integrin α3, integrin β4, and/or integrin β5.

In the method for analyzing a tongue cancer tissue specimen of the present invention, the reference gene may be a housekeeping gene, a cytoskeletal molecule gene, an anchor protein gene, and/or an extracellular matrix gene.

In the method for analyzing a tongue cancer tissue specimen of the present invention, the reference gene may be ACTB.

In the method for analyzing a tongue cancer tissue specimen of the present invention, the reference gene may be KRT5.

In the method for analyzing a tongue cancer tissue specimen of the present invention, the reference gene may be JUP and/or PXN.

In the method for analyzing a tongue cancer tissue specimen of the present invention, the tongue cancer may be tongue squamous cell carcinoma.

The present invention provides a kit for analyzing a tongue cancer tissue specimen, comprising: primer pair(s) for measuring mRNA quantity of one or a plurality of integrin family gene(s) selected from the group consisting of integrin α3, integrin β4, and integrin β5, in the tongue cancer tissue specimen; primer pair(s) for measuring mRNA quantity of one or a plurality of reference gene(s) selected from the group consisting of ACTB, KRT5, JUP, and PXN, in the tongue cancer tissue specimen; and an instruction manual which explains the method for analyzing a tongue cancer tissue specimen of the present invention.

The present invention provides a kit for analyzing a tongue cancer tissue specimen, comprising: a set of primer pairs for measuring mRNA quantity of one or a plurality of pair(s) of an integrin family gene and a reference gene selected from the group consisting of integrin α3/KRT5, integrin α3/JUP, integrin β4/JUP, integrin β4/KRT, integrin β5/ACTB, and integrin β5/PXN, in the tongue cancer tissue specimen; and an instruction manual which explains the method for analyzing a tongue cancer tissue specimen of the present invention.

The present invention provides a kit for analyzing a tongue cancer tissue specimen, comprising: probe(s) for measuring mRNA quantity of one or a plurality of integrin family gene(s) selected from the group consisting of integrin α3, integrin β4, and integrin β5, in the tongue cancer tissue specimen; probe(s) for measuring mRNA quantity of one or a plurality of reference gene(s) selected from the group consisting of ACTB, KRT5, JUP, and PXN, in the tongue cancer tissue specimen; and an instruction manual which explains the method for analyzing a tongue cancer tissue specimen of the present invention.

The present invention provides a kit for analyzing a tongue cancer tissue specimen, comprising: primer pairs for measuring mRNA quantity of one or a plurality of pair(s) of an integrin family gene and a reference gene selected from the group consisting of integrin α3/KRT5, integrin α3/JUP, integrin β4/JUP, integrin β4/KRT, integrin β5/ACTB, and integrin β5/PXN, in the tongue cancer tissue specimen; and an instruction manual which explains the method for analyzing a tongue cancer tissue specimen of the present invention.

According to the method for determining a tongue cancer of the present invention, expression levels, that is, mRNA quantity of an integrin to family gene and a reference gene in the tongue cancer tissue specimen are measured. Then based on their ratio, the malignancy of the tongue cancer, in particular, tongue squamous cell carcinoma can be objectively and accurately determined. According to the method for analyzing a tongue cancer tissue specimen, a ratio of the mRNA quantity of the integrin family gene/the mRNA quantity of the reference gene in the tongue cancer tissue specimen is correlated with clinical data, and thereby useful analysis can be performed for objective and accurate determination of the malignancy of tongue cancer, in particular tongue squamous cell carcinoma. The kit for analyzing a tongue cancer tissue specimen of the present invention enables useful analysis for objective and accurate determination of the malignancy of tongue cancer, in particular, tongue squamous cell carcinoma.

By so doing, for the cases determined to carry clinically poor prognosis from data, the cancer reference rate can be improved by executing an intensive therapeutic regimen such as higher-dose chemotherapy/radiation therapy before and after the operation, more extensive resection during the operation, and more careful consideration of various test results in the course of pre- and post-operational observation, even though they would have been conventionally determined to carry clinically good prognosis. As for cases determined to carry good prognosis, the optimum medical service can be provided to every patient by avoiding excessive treatment/examination.

Moreover, since highly accurate determination can be achieved by including the results of examination at the gene level, the burden on the patient such as medical expense and mental anxiety, can be alleviated. As a result, it is possible to reduce the medical cost in the society as a whole, by proper medical care.

DETAILED DESCRIPTION OF THE INVENTION

Figure 1:
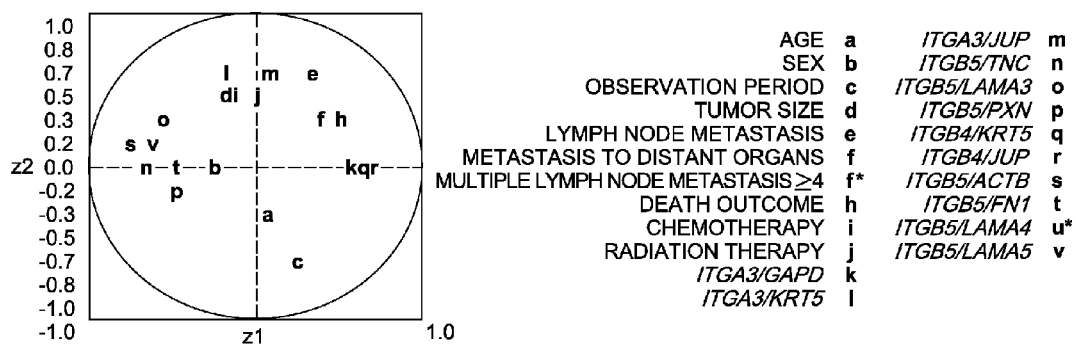
FIG. 1 is a scatter plot of factor loadings of respective variables with respect to the first principal component and the second principal component in principal component analysis in Example 1 of the present invention.

Following is a detailed description of the present invention.

The method for determining a tongue cancer of the present invention comprises measuring the expression level, that is, the mRNA quantity of an integrin family gene in the tongue cancer tissue specimen, and determining the malignancy of tongue cancer, with use of numeric values obtained through normalization of the mRNA quantity of the integrin family gene based on a ratio of the mRNA quantity of the integrin family gene/the mRNA quantity of the reference gene.

In addition, the integrin family gene is ITGA3, ITGB4, and/or ITGB5.

Moreover, the measurement of the mRNA quantity of an integrin family gene is not limited to a particular method, although real-time PCR analysis is more preferably employed. For the measurement of the mRNA quantity of the present invention, Northern blot analysis or solid phase hybridization analysis may also be used. The solid phase hybridization analysis includes, but is not limited to, multi-array hybridization in which mRNA or mRNA-derived labeled nucleic acids are hybridized to an array having two-dimensionally aligned probes for different genes, and bead hybridization in which mRNA or mRNA-derived labeled nucleic acids are hybridized to beads immobilized with probes for different genes.

In order to perform the method for determining a tongue cancer of the present invention, cDNA is synthesized by extracting RNA from a part of tongue cancer tissue. With the cDNA as a template, a group of integrin family genes are subjected to quantitative real-time PCR gene expression analysis using a TaqMan (registered trademark) probe. Next, various reference genes are also subjected to the gene expression analysis for use in the same experiment. Then, the mRNA quantity of ITGA3, ITGB4, and ITGB5 is normalized with the mRNA quantity of the various reference genes as denominators, to yield numerical data. The numerical data obtained through this normalization are used to determine the malignancy of the tongue cancer. In this manner, based on the ratio of mRNA quantity of the integrin gene/mRNA quantity of the reference gene, biological/clinical properties of cancer can be accurately understood and predicted for use in the clinical diagnosis of tongue cancer.

The reference gene is a housekeeping gene, a cytoskeletal molecule gene, an anchor protein gene, and/or an extracellular matrix gene.

Of these, ACTB is preferably used for the reference gene.

Of these, KRT5 is also preferably used for the reference gene.

Of these, JUP and/or PXN is (are) also preferably used for the reference gene.

The primer pairs for use in the present invention to measure the mRNA quantity of integrin family genes and/or reference genes by means of real-time PCR analysis can be designed on the basis of cDNA nucleotide sequences for respective genes available from the homepages of the DNA Data Bank of Japan (DDBJ) of the National Institute of Genetics, and other organizations, by those having ordinary skill in the art with well-known techniques.

The probes for use in the present invention to measure the mRNA quantity of integrin family genes and/or reference genes by means of Northern blot analysis or solid phase hybridization analysis can be designed on the basis of cDNA nucleotide sequences for respective genes available from the homepages of the DNA Data Bank of Japan (DDBJ) of the National Institute of Genetics, and other organizations, by those having ordinary skill in the art with well-known techniques.

In this manner, through the method for determining a tongue cancer of the present invention, the malignancy of tongue cancer, in particular tongue squamous cell carcinoma, can be more objectively and accurately determined.

Following is a detailed description of the present invention, with reference to Examples of the present invention. However, the present invention is not to be considered as being limited by these Examples. The experimental methods and the like in Example 1 are as follows.

(Subject Cases)

The tumor specimens that were used for the gene expression analyses were collected at the time of biopsy or surgical resection from 66 patients with tongue cancer who were treated at the Dental Department of Niigata University Medical and Dental Hospital, the Division of Oral Surgery of Nagaoka Red Cross Hospital, and the Special Dental Care and Oral Surgery of Shinsyu University Hospital from 1999 to 2005. All subjects had been histologically diagnosed as squamous cell carcinoma. The TNM classification, type of invasion (Y-K grade), and other detailed data are shown in Table 1. The study protocol for this research in the present invention was approved by the ethics committee of the Dental Department of Niigata University Medical and Dental Hospital. The study was executed in compliance with the contents of the Ethical Guideline for Clinical Research published by the Ministry of Education, Culture, Sports, Science, and Technology of Japan. As for the participation to this study, the patients were explained the gist of this study and, when informed consents were obtained, letters of written consent were prepared

TABLE 1

Properties of 66 Patients with Squamous Cell Carcinoma of the Tongue

| Property | No. of patients (%) |
|---|---|
| Age | Average 62.38 (range 21-91) |
| Sex | Male 41 (62%) |
| | Female 25 (38%) |
| Observation Period | 115-1821 days (Average 795) |
| Tumor Size (mm) | |
| <20 | 20 (30%) |
| 20-40 | 32 (48%) |
| ≧40 | 14 (21%) |
| Cervical Lymph Node Metastasis | |
| Negative | 31 (47%) |
| Positive | 35 (53%) |
| Distant Metastasis | |
| Negative | 60 (91%) |
| Positive | 6 (9%) |
| Local Recurrence | |
| Negative | 64 (97%) |
| Positive | 2 (3%) |
| Chemotherapy | |
| − | 43 (65%) |
| + | 23 (35%) |
| Radiotherapy | |
| − | 39 (59%) |
| + | 27 (39%) |

TABLE 1-continued

Properties of 66 Patients with Squamous Cell Carcinoma of the Tongue

| Property | No. of patients (%) |
|---|---|
| Outcome | |
| Alive | 54 (82%) |
| Dead | 12 (18%) |

(Extraction of RNA)

Cancer tissue specimens were preserved by immersion in RNA Later (Ambion Inc., TE, USA). These cancer tissue specimens were not subjected to any particular dissection, and thus comprised of tumor parenchymal cells and various stroma component cells such as fibroblasts, vascular endothelial cells, and inflammatory cells. The extraction of total RNA was performed after homogenization with an Ultra-TurraxT8 (IKA Labortechinik, Staufen, Germany) in TRIzol reagent (Invitrogen Corp., Carlsbad, Calif., USA) according to the standard protocol for the reagent, with two rounds of additional phenol precipitation treatments (PCI, Sigma Aldrich, St. Louis, USA). Synthesis of single-strand cDNA was performed by reverse transcription reaction using 2 μg of total RNA as a template (Super Script II, Invitrogen Corporation, Carlsbad, Calif., USA; according to the standard protocol).

(Relative Gene Expression Quantification by Real-Time PCR)

Gene expression analysis was performed by quantitative real-time PCR (Smart Cycler; Cepheid, Sunnyvale, Calif., USA) using the cDNA synthesized from the tongue squamous cell carcinoma tissue as a template. The real-time monitoring with a TaqMan (registered trademark) probe (TaqMan (registered trademark) Gene Expression Assays; Applied Biosystems, CA, USA) was performed in a TaqMan (registered trademark) Universal PCR Master Mix (Applied Biosystems) according to the ABI's standard protocol (600 seconds at 95° C., followed by thermal cycles of 15 seconds at 95° C. and 60 seconds at 60° C.). Several dilution series (1:10:100:1000:10,000:100,000) of template cDNA of a standard tongue cancer tissue were prepared, and respective dilution samples were subjected to real-time PCR according to the same protocol, to thereby make a standard curve of each gene. The mRNA quantity of each gene was quantified based on each standard curve obtained from the threshold cycle (Ct value).

Genes selected to be analyzed are listed in Table 2: eleven ITG family genes, three so-called housekeeping genes (HKG); seven extracellular matrix (ECM) genes including ITG-ligands; and four genes which encode molecules acting in the cytoplasm side of ITG receptors and which consist of so-called anchor protein (ANK) genes and a cytoskeletal molecule (CSK) gene.

TABLE 2

Analyzed Genes

| Functional Category | Gene No. | Probe* |
|---|---|---|
| Integrin Family | ITGA1 | Hs01673837_m1 |
| | ITGA2 | Hs00985382_g1 |
| | ITGA3 | Hs00233722_m1 |
| | ITGA5 | Hs01547684_m1 |
| | ITGA6 | Hs01041013_m1 |
| | ITGAv | Hs00233790_m1 |
| | ITGB1 | Hs00559595_m1 |
| | ITGB3 | Hs00173978_m1 |

TABLE 2-continued

Analyzed Genes

| Functional Category | Gene No. | Probe* |
|---|---|---|
| | ITGB4 | Hs01103172_g1 |
| | ITGB5 | Hs00174435_m1 |
| | ITGB6 | Hs00982346_m1 |
| Housekeeping Gene | ACTB | Hs99999903_m1 |
| | GAPD | Hs99999905_m1 |
| | 18sRNA | Hs99999901_s1 |
| Cytoskeletal Molecule | KRT5 | Hs00361185_m1 |
| Anchor Protein | JUP | Hs00158408_m1 |
| | PLEC1 | Hs0095420_g1 |
| | PXN | Hs00236046_m1 |
| Extracellular Matrix | LAMA3 | Hs01125432_m1 |
| | LAMA4 | Hs00935293_m1 |
| | LAMA5 | Hs00966637_m1 |
| | TNC | Hs00233648_m1 |
| | FN1 | Hs015499-0_g1 |
| | COL1A1 | Hs01076775_g1 |
| | VTN | Hs00169863_m1 |

*Analysis ID of TaqMan (registered trademark) Gene Expression Assays of Applied Biosystems (Statistical Analysis)

Respective variables consisting of clinical data and gene expression data were calculated for the average value, standard deviation, skewness, and kurtosis as elementary statistics, followed by the evaluation of distribution patterns. Then, the correlation coefficient matrixes between respective variables were obtained. The expression levels of the eleven ITG family genes mentioned above were normalized with the expression levels of the other fourteen HKG, ECM, ANK, and CSK genes. The numerical data thus obtained were used for univariate analysis by Mann-Whitney U tests to understand the correlations with the presence of cervical lymph node metastasis or death outcome, serving as clinical parameters for the malignancy. Based on this result, variables were selected for the multivariate regression analyses by a stepwise procedure, and ITG gene expression ratios that exhibited high correlations with cervical lymph node metastasis or death outcome ($p \leq 0.01$) were used for the subsequent multivariate analyses. For the clinical parameters, information of age, sex, tumor size in relation to the area of tumor extension, the presence or absence of cervical lymph node metastasis, the number of cervical lymph node metastasis, and distant metastasis as the metastasis-related items, experience of chemotherapy and radiation therapy as the therapy-related information, and death outcome as the clinical course of the subject cases were used.

In the multivariate analyses, all variables were used to review the correlations between variables by principal component analysis. Subsequently, a multivariate logistic regression analysis using cervical lymph node metastasis as a response variable was performed to detect related factors, and the cervical lymph node metastasis predictive model was evaluated. Further, an analysis using death outcome as an endpoint was performed with a Cox's proportional hazards model.

(Histologic Observations)

Histologic observations were made with paraffin-embedded and HE-stained sections prepared from the same tumor specimens that had been used for the gene expression analysis. The specimens were fixed with 10% formalin and prepared according to the ordinary procedures. Using a plurality of markers which had been suggested to exhibit statistically significant correlations with the clinical malignancy, the morphology with respect to the level of these markers was examined along with the clinical course.

EXAMPLE 1

(Statistical Analysis)

1. Univariate Analysis

According to results from the correlation coefficient matrixes between respective variables, relatively high correlations were observed between cervical lymph node metastasis and radiation ($r=0.54$) and between distant metastasis and death outcome ($r=0.67$) among the background factors. Among the ratios of ITG genes, high correlations were observed between: ITGA3/JUP and ITGA3/KRT5 ($r=0.75$); ITGB5/LAMA3 and ITGB5/TNC ($r=0.52$); ITGB4/JUP and ITGA3/GAPD ($r=0.57$); ITGB4/JUP and ITGB4/KRT5 (0.91); ITGB5/ACTB and ITGB5/TNC ($r=0.64$); ITGB5/ACTB and ITGB5/LAMA3 ($r=0.69$); and ITGB5/ACTB and ITGB5/LAMA5 (0.59); and ITGB5/LAMA4 and ITGB5/FN1 ($r=0.60$). In addition, among background factors and genes, a relatively high correlation was observed between death outcome and ITGB4/JUP ($r=0.53$).

The 151 gene expression ratios, calculated through normalization of the eleven ITG gene expression levels with the fourteen relevant genes, were subjected to the Mann-Whitney tests to find out the correlations with the positivity of cervical lymph node metastasis or death outcome. The results are shown in Table 3 and Table 4.

TABLE 3

Gene Expression Ratios Showing Significance for Cervical Lymph Node Metastasis

| | | Integrin | | | | | | | | | | |
|---|---|---|---|---|---|---|---|---|---|---|---|---|
| Denominator | Numerator | α1 | α2 | α3 | α5 | α6 | αv | β1 | β3 | β4 | β5 | β6 |
| Housekeeping | ACTB | ns | ns | ns | ns | ns | ns | ns | ns | ns | ns | ns |
| Genes | GAPD | ns | ns | 0.0118 | ns | ns | ns | ns | ns | ns | ns | ns |
| | 18sRNA | ns | ns | 0.0215 | ns | ns | ns | ns | ns | ns | ns | ns |
| Extracellular | TNC | ns | ns | ns | ns | ns | 0.0276* | ns | ns | ns | 0.0028* | 0.0444* |
| Matrix | FN1 | ns | ns | ns | ns | ns | ns | ns | ns | ns | 0.0120* | ns |
| | COL1A1 | ns | ns | ns | ns | ns | ns | ns | ns | ns | 0.0457* | ns |
| | VTN | ns | ns | ns | ns | ns | ns | ns | ns | ns | 0.0226* | ns |
| | LAMA3 | ns | ns | ns | ns | ns | ns | ns | ns | ns | 0.0039* | ns |
| | LAMA4 | ns | ns | ns | ns | ns | ns | ns | ns | ns | ns | ns |
| | LAM45 | ns | ns | ns | ns | ns | ns | ns | ns | ns | ns | ns |
| Cytoskeletal Molecule | KRT5 | ns | ns | 0.0083 | ns | 0.0444 | ns | ns | ns | 0.0417 | ns | ns |
| Anchor | JUP | ns | ns | 0.0003 | ns | 0.0304 | 0.0241 | ns | 0.0417 | 0.0423 | ns | ns |

TABLE 3-continued

Gene Expression Ratios Showing Significance for Cervical Lymph Node Metastasis

| Denominator | Numerator | Integrin α1 | α2 | α3 | α5 | α6 | αv | β1 | β3 | β4 | β5 | β6 |
|---|---|---|---|---|---|---|---|---|---|---|---|---|
| Protein | PLEC1 | ns | ns | ns | ns | ns | ns | ns | ns | ns | 0.0104* | ns |
|  | PXN | ns | ns | ns | ns | ns | ns | ns | ns | ns | ≤0.0001* | ns | ns: Not Significant. The numeric values represent significant p-values in the Mann-Whitney U test.
*Inverse Correlation
☐ Gene expression ratios showing p ≦ 0.001

TABLE 4

Gene Expression Ratios Showing Significance for Clinical Outcome

| Denominator | Numerator | Integrin α1 | α2 | α3 | α5 | α6 | αv | β1 | β3 | β4 | β5 | β6 |
|---|---|---|---|---|---|---|---|---|---|---|---|---|
| Housekeeping Genes | ACTB | ns | ns | 0.0362* | ns | 0.0191* | ns | 0.0470* | ns | ns | 0.00025* | 0.0491* |
|  | GAPD | ns | ns | ns | ns | ns | ns | ns | ns | ns | ns | ns |
|  | 18sRNA | ns | ns | 0.0347 | ns | ns | ns | ns | 0.0307 | 0.0484 | ns | ns |
| Extracellular Matrix | TNC | ns | ns | ns | ns | ns | ns | ns | ns | ns | 0.0443* | ns |
|  | FN1 | ns | ns | ns | ns | ns | ns | ns | ns | ns | 0.00028* | ns |
|  | COL1A1 | ns | ns | ns | ns | ns | ns | ns | ns | ns | ns | ns |
|  | VTN | ns | ns | 0.0208 | ns | 0.0333 | ns | 0.0409 | ns | ns | ns | ns |
|  | LAMA3 | ns | ns | ns | ns | ns | ns | ns | ns | ns | 0.0126* | ns |
|  | LAMA4 | ns | ns | ns | ns | ns | ns | ns | ns | ns | 0.00056* | ns |
|  | LAMA5 | ns | ns | ns | ns | ns | ns | ns | ns | ns | 0.00086* | ns |
| Cytoskeletal Molecule | KRT5 | ns | ns | ns | ns | ns | ns | ns | ns | 0.0064 | ns | ns |
| Anchor Protein | JUP | ns | 0.0347 | 0.0121 | ns | ns | ns | 0.0218 | ns | 0.0011 | ns | ns |
|  | PLEC1 | ns | ns | ns | ns | ns | ns | ns | ns | ns | 0.0139* | ns |
|  | PXN | ns | ns | ns | ns | ns | ns | ns | ns | 0.0377 | 0.0333* | ns | ns: Not Significant. The numeric values represent significant p-values in the Mann-Whitney U test.
*Inverse Correlation
☐ Gene expression ratios showing p ≦ 0.001

Many gene expression ratios for ITGA3 and ITGB5 exhibited significance for cervical lymph node metastasis. As to the genes for use in normalization, many gene expression ratios normalized with KRT5 and JUP exhibited significance. An overall tendency is recognized that, as the expression levels of the ITG family genes, the group of ECM genes and the anchor protein PXN become higher, a tumor is more likely characterized to be malignant in terms of lymph node metastasis and death outcome. Only ITGB5 showed a decreased tendency in the expression level along with clinical malignancy. As a result, ITGB5 is expected to show significance with ECM molecule and anchor protein genes whose transcriptional levels are increased with malignancy. An accumulation of significance was observed among the gene expression ratios for ITGB4 and ITGB5 on the death outcome. From these results, ITGA3/GAPD, ITGA3/KRT5, ITGA3/JUP, ITGB4/KRT5, ITGB4/JUP, ITGB5/ACTB, ITGB5/FN1, ITGB5/TNC, ITGB5/LAMA3, ITGB5/LAMA4, ITGB5/LAMA5, and ITGB5/PXN which exhibited p-values of less than 1% with respect to cervical lymph node metastasis or death outcome, were used for the multivariate analysis.

2. Multivariate Analysis

Principal Component Analysis: In the results of principal component analysis using clinical data and the gene expression data as variables, the first through seventh principal components displayed eigenvalues of 1 or more, and their cumulative proportion of variance reached 72.9%. The first, second, and third principal components each included two or more variables with factor loadings of 0.5 or more and eigenvalues 2 or more (Table 5).

TABLE 5

Principal Component Analysis With Clinical Parameters and the Twelve Gene Expression Ratios

|  | Z-1 | Z-2 | Z-3 |
|---|---|---|---|
| Eigenvalue | 5.164 | 3.147 | 2.173 |
| Proportion of variance | 0.235 | 0.143 | 0.099 |
| Cumulative Proportion of Variance | 0.235 | 0.378 | 0.477 |
| Factor loading |  |  |  |
| Age | 0.087 | −0.275 | 0.430 |
| Sex | −0.237 | −0.044 | 0.338 |
| Observation Period | 0.287 | −0.585 | −0.377 |
| Tumor Size (Major Width of Tumor) | −0.159 | 0.430 | −0.192 |
| Cervical Lymph Node Metastasis | 0.398 | 0.674 | −0.032 |
| Distant Metastasis | 0.455 | 0.323 | 0.544 |
| Multiple Cervical Lymph Node Metastasis ≧ 4 | 0.418 | 0.314 | 0.214 |
| Death outcome | 0.555 | 0.347 | 0.566 |
| Chemotherapy | −0.120 | 0.554 | −0.481 |
| Radiotherapy | 0.057 | 0.519 | −0.174 |
| ITGA3/GAPD | 0.644 | 0.079 | −0.089 |
| ITGA3/KRT5 | −0.157 | 0.691 | −0.210 |
| ITGA3/JUP | 0.092 | 0.623 | −0.166 |
| ITGB5/TNC | −0.691 | 0.044 | 0.299 |
| ITGB5/LAMA3 | −0.537 | 0.338 | 0.265 |
| ITGB5/PXN | −0.529 | −0.236 | 0.321 |
| ITGB4/KRT5 | 0.707 | 0.073 | 0.355 |
| ITGB4/JUP | 0.778 | 0.007 | 0.338 |
| ITGB5/ACTB | −0.745 | 0.228 | 0.295 |
| ITGB5/FN1 | −0.514 | 0.075 | 0.141 |

TABLE 5-continued

Principal Component Analysis With Clinical Parameters
and the Twelve Gene Expression Ratios

|  | Z-1 | Z-2 | Z-3 |
|---|---|---|---|
| ITGB5/LAMA4 | −0.538 | 0.266 | 0.109 |
| ITGB5/LAMA5 | −0.649 | 0.107 | 0.262 |

*The underline indicates the most significant clinical factors for each principle component.

For the first principal component (Z-1), the respective gene expression ratios of ITGB3 to 5 and death outcome displayed factor loadings of large absolute values. Large positive values were detected in gene expression data of ITGB4/JUP, ITGB4/KRT5, and ITGA3/GAPD, and large negative values were detected in gene expression data of ITGB5/ACTB and ITGB5/LAMA5. For the second principal component (Z-2), the gene expression ratios of ITGA3 and the presence or absence of cervical lymph node metastasis displayed high factor loadings. In contrast to the first principal component which reflected death outcome, ITGA3/JUP and ITGA3/KRT5 independently displayed high factor loadings of positive values among the ITG gene expression ratios, and the tumor major width (size) and chemotherapy also displayed relatively high factor loadings. For the third principal component (Z-3), while no ITG gene expression ratios displayed high values, distant metastasis and death outcome displayed high factor loadings, which suggest that this component reflects correlations between clinical parameters. For this third principal component, chemotherapy displayed a factor loading of a large negative value.

From a scatter plot of the factor loading of the first principal component and the second principal component it could be interpreted that, as described above, the first principal component along the horizontal axis Z-1 served as a factor axis of genes related to "death outcome" and the second principal component along the vertical axis Z-2 served as a factor axis of genes related to "cervical lymph node metastasis" (FIG. 1). On the factor axis reflecting death outcome (horizontal axis Z-1), factor loadings of positive values exhibiting correlation were found in the group of ITGB4 and ITGA3 gene expression ratios, while factor loadings of negative values exhibiting inverse correlation consisted of ITGB5 gene expression ratios. These gene expression ratios were respectively distributed in the left and right hemispheres in the diagram. On the other hand, on the factor axis reflecting cervical lymph node metastasis (vertical axis Z-2), many ITG gene expression ratios were distributed around zero, among which only ITGA3/JUP and ITGA3/KRT5 were distributed in a factor loading zone equivalent to that of a stage of cervical lymph node metastasis. In addition, the tumor major width (size) was close to the factor of cervical lymph node metastasis on the second principal component (vertical axis), but was positioned in a factor loading zone of relatively small absolute value on the first principal component (horizontal axis).

Multivariate Logistic Regression Analysis with Cervical Lymph Node Metastasis: On the basis of the results of univariate analysis and principal component analysis, multivariate logistic regression analysis was performed with the presence or absence of cervical lymph node metastasis as a response variable. As a result, ITGA3/JUP and ITGB5/PXN were detected as significantly influential factors for cervical lymph node metastasis (Table 6).

TABLE 6

Multivariate Logistic Regression Analysis with Cervical
Lymph Node Metastasis as Response Variable

|  | B | Standard error | P-value | Odds Ratio |
|---|---|---|---|---|
| ITGA3/JUP | 4.013 | 1.733 | 0.021 | 55.287 |
| ITGB5/PXN | −2.095 | 1.023 | 0.041 | 0.123 |
| Invariable | 0.227 | 0.582 | 0.697 | 1.255 |

Of the two ratios, the ITGA3//JUP ratio had a positive correlation, and the ITGB5/PXN ratio had a negative correlation with cervical lymph node metastasis. Of these, the ITGA3/JUP ratio showed the largest values in the partial regression coefficient and the odds ratio. In the predictive accuracy evaluation of the presence of cervical lymph node metastasis, this model showed a true positive rate of 74.3%, a true negative rate of 71.0%, and an accuracy of 72.7% (Table 7).

TABLE 7

Predictive Accuracy of Cervical Lymph Node Metastasis Model

|  |  | Predictive Value (cervical LN metastasis*) | |  |
|---|---|---|---|---|
|  |  | 0** | 1*** |  |
| Observation Value | Cervical LN Metastasis | 0 | 22 | 9 | 71.0 |
|  |  | 1 | 9 | 26 | 74.3 |
|  |  |  |  |  | 72.7 |

*Cervical lymph node metastasis,
**Negative,
***Positive

Cox's Proportional Hazards Model for Survival/Death outcome: The regression analysis with a Cox's proportional hazards model using the outcome, that is, Survival or death, as an endpoint, showed that the ITGB4/JUP ratio was identified as a significantly influential factor of death outcome (Table 8).

TABLE 8

Proportional Hazard Model for Outcome

|  | Logistic regression coefficient β | Standard Error | Level of Significance | Hazard Ratio | 95% CI for Exp(B) | |
|---|---|---|---|---|---|---|
|  |  |  |  |  | Lower limit | Upper limit |
| ITGB4/JUP | 13.87 | 3.98 | 0.00049 | 1,055,671.009 | 432.17 | 2,578,695,704 |

Figure 2:
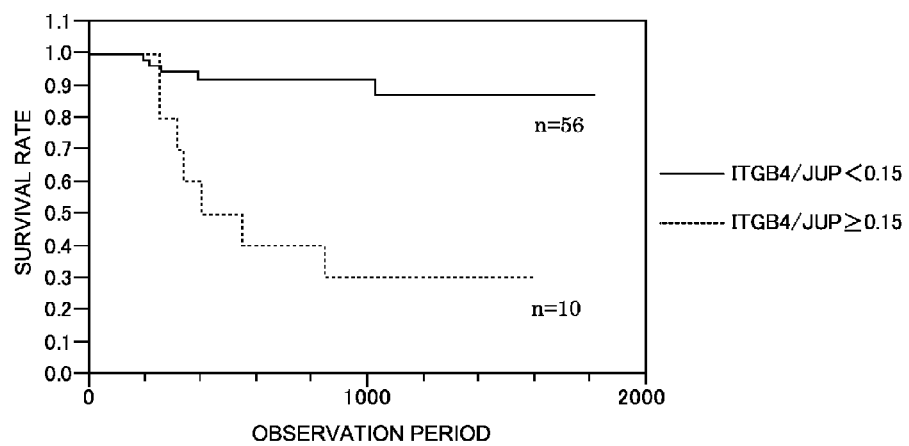
FIG. 2 is a graph showing Kaplan-Meier survival curves between two tongue squamous cell carcinoma tissue groups showing high and low ITGB4/JUP ratios using a Cox's proportional hazards model in Example 1 of the present invention.

The optimum cut-off value of ITGB4/JUP was set with reference to a ROC curve; then, a survival curve was calculated according to the Kaplan-Meier method for the groups with ITGB4/JUP ratios above and below the cut-off value (FIG. 2). In the log-rank test and the Wilcoxon test regarding the survival function between these two groups, the group with ITGB4//JUP ratios less than 0.15 had higher survival rates than the group with ITGB4/JUP ratios more than 0.15, with significant difference of p-values less than 0.1% in both tests.

(Histologic Observations on the Basis of Gene Expression Analysis Results)

Case selection was performed on the basis of ITGB4/JUP and ITGA3/JUP ratios from the results of the gene expression analysis. Tumors presenting high ITGB4/JUP ratios often ended up with multiple cervical lymph node metastasis, followed by distant metastasis, and death outcome. Even some surviving cases followed the course presenting clinical malignancy such as secondary cervical metastasis after the primary tumor dissection. Although not all the histologic observations were consistent, the histologic characteristic was such that expansive invasions of single cells from small cell nests were observed only in tumors with high ITGB4//JUP ratios. The degree of cell differentiation ranges from low-differentiated level to the mixed feature consisting of well-differentiated and low-differentiated tumor cells. Although it is difficult to interpret the image of tumor invasion in cases with extensive inflammatory cell infiltration, prominent invasion was consistently observed at the tumor invasive forefront, which was histologically considered to be highly malignant. Among tumors with high ITGA3/JUP ratios, invasive growth of small cell nests was mainly observed. Distant metastasis was observed only in cases with high ITGB4/JUP ratios. In terms of the degree of cell differentiation, although well-differentiated to low-differentiated regions were mixed, they seemed to be more differentiated in general compared with tumors presenting high ITGB4/JUP ratios. Compared to tumors presenting high ITGB4/JUP ratios that consisted of undifferentiated and relatively homogeneous tumor cells without showing to any epithelial character, there was a generally consistent histologic tendency that invasion was observed at each of the small tumor cell nest, although the cellular atypia of the tumor cell was rather widely varied. By histologic observation of tumors in which both ITGB4/JUP and ITGA3/JUP were low, no invasion was found, and basic characters of the epithelial tissue were found to be intact, with the basement membrane structure and the intercellular bridge structure.

Discussion

With the purpose of establishing an accurate malignancy determination system on the basis of gene expression levels in tongue cancer tissue, eleven ITG genes which encode α and β subunits of ITG receptors were examined as candidate biomarker genes. Statistical processing of the gene expression data indicated the possibility that three of them, namely, ITGA3, ITGB4, and ITGB5 may highly reflect the clinical course of tongue cancer. Statistically, expression levels of all ITG genes showed association with the occurrence of lymph node metastasis, and correlation with histologic malignancy to some extent. Considering the results of the study of the present invention, it is notable that two types of lymph node metastasis were found in the course of tongue cancer: one type that is clinically controllable at the level of cervical lymph node metastasis; and the other type that is deeply associated with death outcome following distant metastasis. The possibility has been shown in which the former type can be defined by the ITGA3 gene expression level and the latter type can be defined by the ITGB4 and ITGB5 gene expression levels.

For the quantitative gene expression analysis performed by the inventors of the present invention, the entire tumor tissue collected at the time of biopsy or surgical resection has been used without separation of cell components. Therefore, it was difficult to obtain the gene specimens with identical quality at the initial stage. The premise is that the collected gene specimens are of varied quality as to degradation level, tissue composition, and dissected sites. Under such a circumstance, some trick for extracting clinically useful information on the gene expression was considered to be practically inevitable. Conventionally, so-called normalization, or, calculation of the ratios of the target gene expression to ubiquitously expressed housekeeping genes (HKG) has been performed as an efficient method for comparing the results from quantitative gene expression analyses under different conditions. Nevertheless, as the quantitative real-time PCR comes to be commonly used, it has been pointed out that HKG genes are not always appropriate for normalization, because their expression levels have a large variation among types of tissue or locations of dissected site within a tissue. In addition to such a background, variation occurs in the expression levels of ITG family genes which show characteristic localization in squamous cell carcinoma (SCC) tissue-component cells such as epithelial cells, tumor cells, fibroblasts, and inflammatory invasive cells. With a purpose of selecting sets of genes capable of efficient extraction of various ITG family gene expression levels, an attempt was made to normalize them with a plurality of gene expressions. In addition to HKG, normalization was attempted with a number of intercellular stroma genes constituting extracellular matrix (ECM), cytoskeletal molecule genes (CSK), and anchor protein genes (ANK) based on the co-localization and/or functional relevance with ITG molecules. As a result, univariate analysis with the Mann-Whitney test detected that ITGA3, ITGB4, and ITGB5 data normalized with KRT5, JUP, and PXN exhibited high significance for cervical lymph node metastasis and death outcome. ITGA3 and ITGB4 are molecules localized mainly in the epithelium of oral mucous membrane. For their normalization, KRT5 and JUP were shown to have a potential to be used as normalization molecules for comparison of gene expression data among cases. KRT5 and JUP function as ANKs which connect CSKs of epithelial cells, as well as adhesion molecules on the cell membrane including ITG, cadherin and others, to intracellular filaments. The presented statistical significance remains to be validated with functional support by detailed examination of the localization of these molecules in the future.

Principal component analysis was proved to be useful for comprehensively evaluating the correlation between factors from various aspects. For the first principal component which reflected death outcome, ITG gene expression ratios represented by ITGB4/JUP and ITGB5//ACTB, as well as distant metastasis and multiple cervical lymph node metastasis, displayed factor loadings of large absolute values. This means that these ITG gene expression levels are positively or negatively correlated with death outcome. For the second principal component which reflects cervical lymph node metastasis, on the other hand, only the ITGA3/KRT5 and ITGA3/JUP ratios displayed high factor loadings, suggesting that these factors associate with formation of cervical lymph node metastasis as independent variables. Correlations between these factors are well represented by a scatter plot of factor loading of the first principal component and the second principal component. The tumor major width (d: Tumor size in FIG. 1) was positioned in a factor loading zone of a relatively large value in the vicinity of the second principal component axis (vertical axis), suggesting that the tumor size is not directly related to death outcome but has some effect upon the formation of cervical lymph node metastasis. Values represented by ITGA3/KRT5 (l) and ITGA3/JUP (m) positioned similarly in the vicinity of the second principal component axis were correlated with the tumor size, but not correlated with death outcome indicated by the first principal component axis (horizontal axis). It can be said that these ratios reflect the probability of cervical lymph node metastasis which is controllable by appropriate treatment such as cervical dissection. Conversely, the probability of lymph node metastasis defined by the ratio of ITGB4 and ITGB5 gene expression levels on the first principal component axis is related to cervical lymph node metastasis, in particular, multiple cervical lymph node metastasis (f), as well as being strongly associated with distant metastasis and local recurrence. Therefore, these ITGB4 and ITGB5 values can be considered to be ultimately related to death outcome. The third principal component, similar to the first principal component, represents the factor axis of death outcome and distant metastasis, but displayed a factor loading of large negative value for chemotherapy, meaning that chemotherapy is negatively correlated with distant metastasis and death outcome; in other words, chemotherapy may suppress distant metastasis and death outcome.

Multivariate logistic regression analysis detected the ITGA3/JUP and ITGB5/PXN ratios as significant explanatory variables of cervical lymph node metastasis. The ITGA3/JUP ratio was one of the factors which displayed a tendency of lymph node metastasis unrelated to distant metastasis and death outcome in the results of principal component analysis mentioned above. On the other hand, the ITGB5/PXN ratio was a factor reflecting a factor axis related to distant metastasis or death outcome. Of these, the ITGA3/JUP ratio showed the largest values in the logistic regression coefficient and the odds ratio, indicating that the ITGA3/JUP ratio is highly capable of predicting lymph node metastasis in general. This finding is consistent with the fact that most lymph node metastasis can be suppressed regionally at the cervical lymph node level, and that few are uncontrollable due to distant metastasis and local recurrence.

Thus, the results of multivariate logistic regression analysis also showed that lymph node metastasis could be judged by the summation of effects of two independent metastatic properties. The regression model of cervical lymph node metastasis calculated with these two factors showed the predictive accuracy of cervical lymph node metastasis at a true positive rate of 74.3%, a true negative rate of 71.0%, and an accuracy of 72.7%, which however cannot be said to have satisfied the level required for the clinical practice. Still, considering that lymph node metastasis results from extremely complicated biological actions comprising of various cell components, the accuracy is unexpectedly high for a determination that uses only two factors related to ITG molecules. The next task is to establish an accurate prediction model at a level of practical application by developing a model with various molecule groups related to other biological phenomena in the future.

Only the ITGB4//JUP ratio was detected as a factor associated with death outcome by the Cox's proportional hazards regression model, regardless of the multivariate analysis. This result was consistent with the finding that the ITGB4 and ITGB5 gene expression ratios are distributed around the factor axis which reflects death outcome, or, the first principal component (Z-1) axis, in the scatter plot of factor loadings of the principal component analysis, showing that the ITGB4 and ITGB5 ratios, while being negatively correlated, were determined to be an approximate factor explaining death outcome or distant metastasis. The ITGB4/JUP as a main representing factor thereof, showed the hazard ratio of 1,055, 671 and the p-value of p<0.0001. Similarly, the explanatory power of this factor was also evident in a cumulative survival curve according to the Kaplan-Meier method and the log-rank test.

Conventionally, ITG family members have been relatively often reported on the functions influencing the tumor properties. ITGα3 forms a pair with an ITGβ1 subunit to function as a receptor for stromal molecules in tissues such as fibronectin (FN), laminin-5 composed of LAMA3 (laminin α3β1γ1), laminin-10 composed of LAMA5 (laminin α5β1γ1), and laminin 11 composed of LAMA5 (laminin α5β2γ1). The ITGA3 expression is observed to have a wide distribution mainly in epithelial basal cells, as well as in the lung, uterus, esophagus, renal glomerulus, and the like, and the normal function of ITGα3 is said to include cell adhesion, motility and apoptosis. It is also reported that the expression status of integrin α3β1 having an ITGA3 subunit affects the cancer cell metastasis and the histopathologic grade in uterine cancer and colon cancer. Meanwhile, the ITGB4 expression is also observed in epithelial cells, mesenchymal cells, Schwann cells, vascular endothelial cells, and the like. The integrin α6β4 receptor functions as a receptor for laminin-5. ITGA4 is considered to be involved in not only cell adhesion but also development, cell differentiation and proliferation because its expression is observed during wound healing, neuronal extension and fetal period. ITGB5 is also found in epithelial basal cells, and serves as an subunit of integrin αvβ5 which functions as a receptor for FN and vitronectin. ITGB5 is considered to be involved in cell adhesion, proliferation, motility and visualization in normal cells. Its strong expression is known in highly invasive stomach cancer. Angiogenesis into tumor tissue is an important phenomenon in the development of tumors and occurrence of metastasis. Previous studies have shown that ITGB4 is expressed in vascular endothelial cells as a factor controlling migration and invasion of these cells. It was demonstrated that angiogenesis adjacent to a tumor tissue is remarkably inhibited in ITGB4 knockout mice. On the contrary, ITGβ5 was shown to exhibit the inhibitory effect on the angiogenesis in tumor tissue, as the angiogenesis into the surroundings of tumor cells is enhanced in ITGB5 knockout mice. The study of the present invention indicated that an increase in the ITGB4 expression level and a decrease in the ITGB5 expression level are associated with distant metastasis and death outcome. These integrin gene expression data raise the possibility of reflecting the phenomena of the tumor infiltration into the vasculature and the activated tumor growth due to the activated angiogenesis. These mechanisms need to be scrutinized further in the future.

Conventionally, standard for the prediction of distant metastasis and life prognosis was not clear, because histologic determination had been the only available means. Although the histologic determination could predict tumor malignancy to some extent, it was often difficult to perform reproducible prognosis for the probability of distant metastasis and the outcome based solely on the histologic determination, because, as shown here, tumors classified on the basis of the ITGB4/JUP and ITGA3/JUP ratios exhibit divergent histology. Associations of at least two factors are suggested in the study of the present invention with respect to cervical lymph node metastasis: one is irrelevant to the distant metastasis; and the other is deeply associated with the distant metastasis. Expression data are expected to bring objective information into the most challenging issues related to the therapy of oral cancer. Tongue cancer accounts for about a half of oral cancer cases and tends to metastasize from relatively early stages. Therefore, it is considered to be extremely beneficial to put into practical use of a method that predicts the probability of latent lymph node metastasis and distant metastasis, even at T1-T2 stages of the disease. The study of the present invention, along with previous studies, has indicated the potential of chemotherapy to suppress distant metastasis. Therefore, the treatment regimen based on an accurate understanding of the tumor properties is important for better control rate of cancer. The establishment of a system for providing information regarding the risk of cervical lymph node metastasis and distant metastasis, as well as invasiveness of tumors, would bring about remarkable benefits such as comprehensive advantages, improvements in survival rate and QOL, moderation in medical costs and others.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method for determining a tongue cancer, comprising: measuring mRNA quantity of one or a plurality of pair(s) of an integrin family gene and a reference gene selected from the group consisting of integrin α3/JUP, integrin β4/JUP, and integrin β5/PXN, in the tongue cancer tissue specimen; and determining the malignancy of tongue cancer based on a ratio of the mRNA quantity of the integrin family gene to the mRNA quantity of the reference gene.

2. The method for determining a tongue cancer according to claim 1, wherein said measurement of the mRNA quantity of the integrin family gene is performed by real-time PCR analysis.

3. The method for determining a tongue cancer according to claim 1, wherein said measurement of the mRNA quantity of the integrin family gene and the reference gene is performed by Northern blot analysis or solid phase hybridization analysis.

4. A method for analyzing a tongue cancer tissue specimen, comprising the steps of:
measuring mRNA quantity of one or a plurality of pair(s) of an integrin family gene and a reference gene selected from the group consisting of integrin α3/JUP, integrin β4/JUP, and integrin β5/PXN, in the tongue cancer tissue specimen; and correlating a ratio of the mRNA quantity of the integrin family gene/the mRNA quantity of the reference gene with clinical data.

5. The method for analyzing a tongue cancer tissue specimen according to claim 4, wherein said clinical data is composed of one or a plurality of type(s) of data selected from the group consisting of TNM classification, Y-K grade, response to chemotherapy, response to radiation therapy, and prognosis.

6. The method for analyzing a tongue cancer tissue specimen according to claim 4, wherein said measurement of the mRNA quantity of the integrin family gene and the reference gene is performed by real-time PCR analysis.

7. The method for analyzing a tongue cancer tissue specimen according to either claim 4, wherein said measurement of the mRNA quantity of the integrin family gene and the reference gene is performed by Northern blot analysis or solid phase hybridization analysis.

* * * * *